United States Patent [19]

Tsang

[11] Patent Number: 5,681,795
[45] Date of Patent: Oct. 28, 1997

[54] 3-BENZOYL PYRROLE AND PYRAZOLE HERBICIDES

[75] Inventor: Tsze H. Tsang, El Cerrito, Calif.

[73] Assignee: Zeneca Limited, London, United Kingdom

[21] Appl. No.: 538,678

[22] Filed: Oct. 3, 1995

Related U.S. Application Data

[63] Continuation of Ser. No. 205,218, Mar. 2, 1994, abandoned.

[51] Int. Cl.$^6$ .................. A01N 43/36; C07D 207/323
[52] U.S. Cl. .................. 504/283; 504/287; 548/539; 548/561
[58] Field of Search .................. 504/280, 283, 504/287; 548/374.1, 375.1, 539, 561

[56] References Cited

U.S. PATENT DOCUMENTS

| | | | |
|---|---|---|---|
| 4,002,643 | 1/1977 | Carson | 424/274 |
| 4,863,503 | 9/1989 | Anthony et al. | 504/287 |

OTHER PUBLICATIONS

CA 112:32139z Synergistic herbicides. Goshima et al. 1990.
CA 120:99446f Synergistic herbicides . . . for paddy. Honma et al. 1994.
CA 120:99448h Synergistic herbicides . . . derivatives. Honma et al. 1994.

*Primary Examiner*—Joseph McKane
*Attorney, Agent, or Firm*—Joseph R. Snyder; Joel G. Ackerman

[57] ABSTRACT

Compounds having the formula

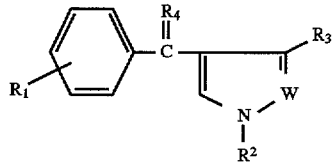

possessing herbicidal activity.

33 Claims, No Drawings

3-BENZOYL PYRROLE AND PYRAZOLE HERBICIDES

This application is a continuation of application Ser. No. 08/205,218, filed Mar. 2, 1994, now abandoned.

FIELD OF THE INVENTION

This invention relates to certain 3-benzoyl pyrrole and pyrazole compounds which demonstrate herbicidal activity.

DESCRIPTION OF THE INVENTION

According to this invention, compounds of the following structure have been found to exhibit herbicidal activity:

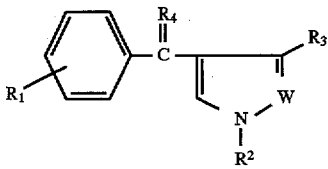

in which $R_1$ is hydrogen, 2- or 3-halo, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, nitro, $C_2$–$C_4$ alkoxyalkyl, phenoxy, 4-chlorophenoxy, 2,3-dihalo, 3,4-dihalo, 2,4-dimethyl, 2,5-di-(trifluoromethyl), 3-methyl-4-halo, one halo and one trifluoromethyl group, or 2-chloro-3-ethoxymethyl-4-methylsulfonyl;

$R_2$ is (a) $C_1$–$C_3$ alkyl; difluoromethyl, $N(CH_3)_2$, acetyl or —$CON(CH_3)_2$; or $R_2$ is hydrogen if $R_1$ is ortho-($C_1$–$C_4$ haloalkyl, $C_1$–$C_4$ haloalkoxy, fluoro or bromo) or is 2-fluoro-3-trifluoromethyl;

$R_3$ is hydrogen, methyl or chloro if $R_2$ is methyl or ethyl; otherwise $R_3$ is hydrogen;

$R_4$ is O or $NOR_5$ where $R_5$ is methyl or ethyl; and

W is (a) —CH, —C(CH$_3$), —CCl, —CBr or N if $R_2$ is methyl, or (b) —CH, —C(CH$_3$) or —CCl if $R_2$ is ethyl; otherwise W is —CH.

"Alkyl", "alkoxy" and the like include both straight and branched chain groups having the indicated number of carbon atoms. "Halo" includes chloro, fluoro, bromo and iodo.

Preferred compounds are those in which (a) $R_1$ is hydrogen, a mono-substituent, dihalo or 2-fluoro-3-trifluoromethyl and $R_2$ is methyl, ethyl or difluoromethyl, and (b) $R_1$ is an ortho- mono-substituent or 2-fluoro-3-trifluoromethyl and $R_2$ is hydrogen.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, as pre- and/or post-emergent herbicides. Pre-emergence herbicides are applied prior to emergence of vegetation from the soil; post-emergence herbicides are applied to control or kill existing vegetation.

Compounds of this invention which are pyrroles may be prepared by reacting a benzoyl chloride or bromide with the appropriate pyrrole.

In general this reaction will produce a mixture of 2- and 3-benzoyl pyrroles, and the 3-benzoyl pyrroles of this invention are obtained by conventional fractionation.

Pyrazoles of this invention may be prepared by reacting a benzoyl chloride or bromide with, for instance 4-bromopyrazole. N-substituted benzoylpyrazoles may then be prepared by using a suitable alkylating agent.

The following are examples of the preparation of compounds of this invention.

EXAMPLE I

Preparation of 3-(3-trifluoromethoxy) benzoyl-1-methyl pyrrole (Compound No. 7 herein)

To a solution of 3-trifluoromethoxybenzoyl chloride (5.0 g., 22.3 mmole) in dichloromethane (50 mL) at room temperature was added a solution of Stannic chloride (1.0M in CH$_2$Cl$_2$, 22.3 mL, 22.3 mmol), and the resulting mixture was stirred for 5 minutes. To this mixture was added a solution of 1-methylpyrrole (2.0 mL, 22.3 mmole) dropwise and the resulting mixture was stirred at room temperature for 18 hours. It was quenched with water (50 mL), washed with brine, dried over sodium sulfate and concentrated to give a brown oil. The crude product was purified by flash chromatography (silica gel, eluted with 10% ethyl acetate-hexane) to give 2 fractions:

(1) 2-(3-trifluoromethoxy)benzoyl pyrrole, 710 mg. and (2) 3-(3-trifluoromethoxy)benzoyl pyrrole, 330 mg.

EXAMPLE II

Preparation of 4-(3-trifluoromethoxy)benzoyl-1-methylpyrazole (Compound 53 herein)

(a) In a flask was placed 1.0 g (6.80 mmol) 4-bromopyrazole. While maintaining the temperature at about –70° C., 6.5 ml (16.3 mmol)n-butyllithium was added by syringe. The reaction mixture was warmed to room temperature, then mixed for 1.5 hours. It was then cooled and 1.5 g (6.80 mmol) 3-trifluoromethoxybenzoyl chloride was added slowly. The reaction mixture was again warmed to room temperature and stirred overnight. It was then quenched with water, extracted with ether and dried. The product was purified by flash chromatography and was spectroscopically identified as 4-(3-trifluoromethoxy) benzoylpyrazole.

(b) Product of stage (a) (0.2 g, 0.778 mmol) was put in a flask and 0.8 ml (0.786 mmol) potassium tert-butoxide was added by syringe. The mixture was stirred 15 minutes, then 0.05 ml (0.786 mmol) methyl iodide was added by syringe. The reaction mixture turned cloudy almost immediately. It was then heated to reflux, then cooled and quenched with water. The precipitate was extracted with ether and dried. There was obtained 140 mg of product, identified as the desired product by spectroscopic analyses.

Table I depicts representative compounds of this invention in which $R_3$ is hydrogen, $R_4$ is O and W is —CH, prepared by a process as described above. Most compounds were obtained as oils. Structures were confirmed by spectroscopic analyses.

TABLE I

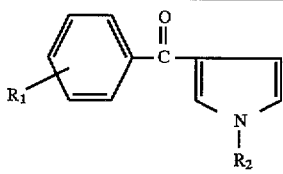

| Compound No. | R₁ | R₂ |
|---|---|---|
| 1 | 3-CH₃ | CH₃ |
| 2 | 2-Cl, 3-C₂H₅OCH₂, 4-CH₃SO₂ | CH₃ |
| 3 | 3-CF₃ | CH₃ |
| 4 | 2,4-CH₃ | CH₃ |
| 5 | 3-CH₃ | C₂H₅ |
| 6 | 3-F, 4-CF₃ | CH₃ |
| 7 | 3-OCH₃ | CH₃ |
| 8 | H | CH₃ |
| 9 | 3-CF₃ | C₂H₅ |
| 10 | 3-OCH₃ | CH₃ |
| 11 | 2-CF₃ | H |
| 12 | 2,5-CF₃ | CH₃ |
| 13 | 2-CF₃ | CH₃ |
| 14 | 3-CH₃, 4-Cl | CH₃ |
| 15 | 2-OCF₃ | H |
| 16 | 2-OCF₃ | CH₃ |
| 17 | 2-F, 3-CF₃ | H |
| 18 | 2-F, 3-CF₃ | CH₃ |
| 19 | 2-F, 5-CF₃ | CH₃ |
| 20 | 3-F | CH₃ |
| 21 | 3-OC₆H₅ | CH₃ |
| 22 | 3-NO₂ | CH₃ |
| 23 | 3-C₂H₅ | CH₃ |
| 24 | 3-Br | CH₃ |
| 25 | 2-OCH₃ | H |
| 26 | 3-C₂H₅OCH₂ | CH₃ |
| 27 | 2-SCH₃ | CH₃ |
| 28 | 2-CH₃ | CH₃ |
| 29 | 2-Br | H |
| 30 | 2-F | H |
| 31 | 2-Cl | CH₃ |
| 32 | 2-Br | CH₃ |
| 33 | 2-F | CH₃ |
| 34 | 3,4-F | CH₃ |
| 35 | 2,3-F | H |
| 36 | 2-F, 3-Cl | H |
| 37 | 2,3-F | CH₃ |
| 38 | 3-Cl | CH₃ |
| 39 | 3-I | CH₃ |
| 40 | 3-OCHF₂ | CH₃ |
| 41 | 3-OCF₃ | N(CH₃)₂ |
| 42 | 3-OCF₃ | C₂H₅ |
| 43 | 3-OCF₃ | n-C₃H₇ |
| 44 | 3-OCF₃ | i-C₃H₇ |
| 45 | 3-OCF₃ | —CON(CH₃)₂ |
| 46 | 3-OCF₃ | —COCH₃ |
| 47 | 3-OCF₃ | CHF₂ |
| 48 | 3-(4-ClC₆H₄O) | CH₃ |

Other compounds of this invention include:

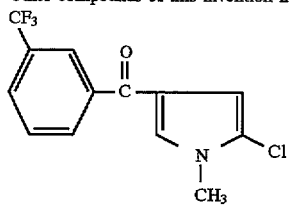

(Compound No. 49)

TABLE I-continued

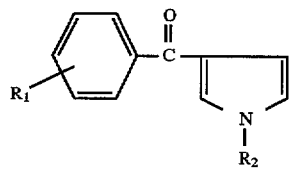

| Compound No. | R₁ | R₂ |
|---|---|---|

(Compound No. 50)

(Compound No. 51)

(Compound No. 52)

(Compound No. 53)

(Compound No. 54)

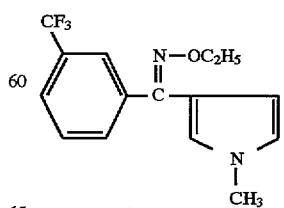

(Compound No. 55)

TABLE I-continued

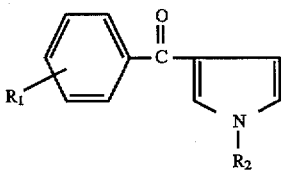

| Compound No. | $R_1$ | $R_2$ |
|---|---|---|

(Compound No. 56) with structure: CF$_3$O-phenyl-C(=N-OC$_2$H$_5$)-pyrrole-N-CH$_3$

Herbicidal Activity Tests

Compounds of Table I were tested for herbicidal activity as follows:

PRE-EMERGENCE HERBICIDAL EVALUATION

On the day preceding treatment, seeds of several different weed species were planted in a sandy loam soil containing only trace organic matter. Propagules were sown in individual rows using one species per row across the width of a flat. The grass weeds planted were green foxtail (*Setaria viridis*), wild oat (*Avena fatua*) and barnyardgrass (*Echinochloa crus-galli*). Broadleaf weeds utilized were wild mustard (*Brassica kaber*), velvetleaf (*Abutilon theophrasti*), and annual morningglory (*Ipomoea* spp.). Additionally, yellow nutsedge (*Cyperus esculentus*) nutlets were sown. Seeding depths ranged from 1.0 to 1.5 cm and plant densities ranged from 3 to 25 plants per row depending on individual plant species.

Solutions of the test compounds were prepared by weighing out 74.7 mg of the test compound into a bottle, then dissolving the compound in 7 ml of acetone containing 1% v/v Tween 20 (polyoxyethylene sorbitan monolaurate emulsifier) as a surfactant and then adding 7 ml of deionized water to reach a 14 ml final volume. Tween 20 content was 0.5% v/v of the final spray volume. Additional solvents, not exceeding 2 ml (15% of spray volume), were used if needed to dissolve the compound.

The soil surface was sprayed inside an enclosed linear spray table with the nozzle set at 30.5 cm (12 inches) above the soil line. The spray table was calibrated to deliver 748 L/ha (80 gal/A) with the application rate being 4 kg/ha. After treatment the flats were placed into a greenhouse and watered overhead by sprinkling. The greenhouse environmental systems provided the plants with natural and artificial (via metal halide lamps) lighting to attain 14 hours of light per day. Day and night temperatures were maintained at 29° and 21° C. respectively.

The degree of weed control was evaluated and recorded 17–21 days after treatment as a percentage of weed control as compared to the growth of the same species of the same age in an untreated control flat. Percent control is the total injury to the plants due to all factors including inhibited emergence, stunting, malformation, chlorosis and other types of plant injury. The control ratings range from 0 to 100 percent, where 0% represents no effect with growth equal to the untreated control and where 100% represents complete kill. A dash indicates that no test was performed at that level of application.

POST-EMERGENCE HERBICIDAL EVALUATION

The soil was prepared and seeded with the same species and methodology described for the pre-emergence test. Post-emergence flats were placed in the greenhouse under the same environmental conditions as described for the pre-emergence flats and watered overhead by sprinkling. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 4 kg/ha. Treated plants were then returned to a greenhouse and watered daily without wetting the foliage. The degree of weed control was evaluated 17 to 21 days after application and recorded as percentage of control as compared to the growth of the same species in an untreated control flat of the same age. The percent control scale (0–100%) used to evaluate the pre-emergence treatment was also applied to the post-emergence treatment.

Results are listed in Table II below, expressed as average control of the three grasses (GR) (wild oat, watergrass, foxtail) and three broadleaf weeds (BL) (morningglory, mustard, velvetleaf), and of nutsedge (NS).

TABLE II

| | % Control, 3.57 kg/ha | | | | | |
|---|---|---|---|---|---|---|
| Compound | Pre-emergence | | | Post-emergence | | |
| No. | GR avg. | BL avg. | NS | GR avg. | BL avg. | NS |
| 1 | 66 | 66 | 10 | 10 | 33 | 5 |
| 2 | 59 | 76 | 10 | 43 | 91 | 10 |
| 3 | 96 | 76 | 85 | 33 | 35 | 60 |
| 4 | 15 | 41 | 0 | 3 | 33 | 0 |
| 5 | 45 | 28 | 5 | 0 | 10 | 5 |
| 6 | 93 | 68 | 80 | 88 | 66 | 85 |
| 7 | 95 | 100 | 85 | 86 | 53 | 90 |
| 8 | 0 | 0 | 0 | 3 | 50 | 0 |
| 9 | 81 | 73 | 40 | 20 | 13 | 30 |
| 10 | 95 | 66 | 85 | 66 | 51 | 85 |
| 11 | 76 | 70 | 60 | 13 | 18 | 10 |
| 12 | 1 | 30 | 0 | 3 | 21 | 0 |
| 13 | 79 | 73 | 50 | 21 | 18 | 20 |
| 14 | 35 | 6 | 0 | 8 | 13 | 5 |
| 15 | 81 | 75 | 70 | 8 | 53 | 15 |
| 16 | 98 | 96 | 100 | 48 | 55 | 70 |
| 17 | 0 | 8 | 0 | 0 | 43 | 0 |
| 18 | 95 | 70 | 85 | 30 | 30 | 30 |
| 19 | 68 | 66 | 15 | 5 | 25 | 5 |
| 20 | 98 | 80 | 90 | 75 | 55 | 80 |
| 21 | 70 | 70 | 0 | 23 | 68 | 10 |
| 22 | 73 | 68 | 60 | 10 | 25 | 5 |
| 23 | 73 | 67 | 60 | 43 | 35 | 60 |
| 24 | 76 | 66 | 60 | 31 | 40 | 30 |
| 25 | 3 | 45 | 0 | 5 | 35 | 0 |
| 26 | 83 | 60 | 65 | 56 | 60 | 75 |
| 27 | 73 | 70 | 80 | 31 | 45 | 50 |
| 28 | 86 | 73 | 85 | 41 | 73 | 50 |
| 29 | 51 | 31 | 10 | 0 | 6 | 0 |
| 30 | 16 | 46 | 0 | 1 | 23 | 0 |
| 31 | 86 | 71 | 85 | 68 | 78 | 85 |
| 32 | 88 | 73 | 80 | 23 | 61 | 50 |
| 33 | 95 | 80 | 85 | 56 | 70 | 80 |
| 34 | 80 | 65 | 50 | 63 | 48 | 60 |
| 35 | 6 | 26 | 0 | 1 | 33 | 0 |
| 36 | 96 | 76 | 85 | 92 | 73 | 90 |
| 37 | 96 | 83 | 90 | 98 | 75 | 90 |
| 38 | 96 | 70 | 85 | 92 | 86 | 90 |
| 39 | 83 | 72 | 50 | 56 | 63 | 60 |
| 40 | 90 | 76 | 80 | 96 | 76 | 90 |

TABLE II-continued

| | % Control, 3.57 kg/ha | | | | | |
|---|---|---|---|---|---|---|
| Compound | Pre-emergence | | | Post-emergence | | |
| No. | GR avg. | BL avg. | NS | GR avg. | BL avg. | NS |
| 41 | 36 | 36 | 0 | 5 | 16 | 5 |
| 42 | 83 | 75 | 15 | 20 | 18 | 5 |
| 43 | 30 | 26 | 0 | 10 | 18 | 5 |
| 44 | 21 | 35 | 0 | 6 | 15 | 5 |
| 45 | 33 | 36 | 0 | 8 | 15 | 5 |
| 46 | 38 | 50 | 0 | 5 | 16 | 5 |
| 47 | 43 | 68 | 0 | 11 | 26 | 5 |
| 48 | 48 | 71 | 0 | 11 | 66 | 10 |
| 49 | 53 | 6 | 0 | 6 | 23 | 0 |
| 50 | 45 | 40 | 10 | 5 | 11 | 5 |
| 51 | 58 | 5 | 5 | 6 | 20 | 0 |
| 52 | 38 | 55 | 5 | 11 | 33 | 5 |
| 53 | 68 | 66 | 70 | 13 | 65 | 5 |
| 54 | 11 | 16 | 0 | 0 | 31 | 5 |
| 55 | 83 | 70 | 70 | 16 | 23 | 30 |
| 56 | 61 | 55 | 0 | 6 | 15 | 10 |

*Application rate - 2.7 kg/ha

In practice, a pure compound can be used as an herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrene-butadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Oil | |
|---|---|
| Ingredient | Weight % |
| Active Compound | 1 |
| Oil solvent-heavy aromatic naphtha | 99 |
| Total | 100 |

| Emulsifiable Concentrate | |
|---|---|
| Active Compound | 50 |
| Kerosene | 45 |

| -continued | | | |
|---|---|---|---|
| Emulsifying agent (mixture of long chain ethoxylated polyethers with long chain sulfonate) | 5 | | |
| Total | 100 | | |

| Emulsifiable Concentrate | |
|---|---|
| Active Compound | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

These compounds are preferably employed in combination with a safener such as 2,2-dichloro-N,N-di-2-propenylacetamide (dichlormid).

What is claimed is:

1. A compound having the formula

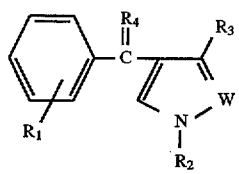

in which $R_1$ is hydrogen, 2- or 3-halo, $C_1-C_4$ alkyl, $C_1-C_4$ haloalkyl, $C_1-C_4$ alkoxy, $C_1-C_4$ haloalkoxy, $C_1-C_4$ alkylthio, $C_1-C_4$ haloalkylthio, nitro, $C_2-C_4$ alkoxyalkyl, phenoxy, 4-chlorophenoxy, 2,3-dihalo, 3,4-dihalo, 2,4-dimethyl, 2,5-di-(trifluoromethyl), 3-methyl-4-halo, one halo and one trifluoromethyl group, or 2-chloro-3-ethoxymethyl-4-methylsulfonyl;

$R_2$ is
(a) $C_1-C_3$ alkyl; difluoromethyl, $N(CH_3)_2$, acetyl or —$CON(CH_3)_2$; or
(b) $R_2$ is hydrogen if $R_1$ is ortho-($C_1-C_4$ haloalkyl, $C_1-C_4$ haloalkoxy, fluoro or bromo) or is 2-fluoro-3-trifluoromethyl;

$R_3$ is hydrogen, methyl or chloro if $R_2$ is methyl or ethyl; otherwise $R_3$ is hydrogen;

$R_4$ is O or $NOR_5$ where $R_5$ is methyl or ethyl and

W is
(a) —CH, —CCl or —CBr if $R_2$ is methyl, or
(b) —CH, or —CCl if $R_2$ is ethyl; otherwise W is —CH; with the proviso that when $R_2$ is methyl, W is CH, $R_3$ is hydrogen and $R_4$ is O, $R_1$ is not hydrogen.

2. A compound according to claim 1 in which $R_2$ is methyl, ethyl or difluoromethyl.

3. A compound according to claim 2 in which $R_1$ is halo, $C_1-C_4$ alkyl, $C_1-C_4$ haloalkyl, $C_1-C_4$ alkoxy, $C_1-C_4$ haloalkoxy, $C_1-C_4$ alkylthio, $C_1-C_4$ haloalkylthio, nitro, phenoxy, $C_2-C_4$ alkoxyalkyl, phenoxy, 4-chlorophenoxy, 2,3-dihalo, 3,4-dihalo, or one halo and one trifluoromethyl group.

4. A compound according to claim 2 in which $R_1$ is halo, methyl, trifluoromethyl, trifluoromethoxy, methoxy, nitro, ethoxymethyl, dihalo or one halo and one trifluoromethyl group.

5. A compound according to claim 1 in which $R_2$ is hydrogen.

6. A compound according to claim 5 in which $R_1$ is 2-methyl, 2-trifluoromethyl, 2-methoxy, 2-trifluoromethoxy, 2-fluoro, 2-bromo or 2-fluoro, 3-trifluoromethyl.

7. A compound according to claim 1 in which W is —CH and $R_4$ is O.

8. A compound according to claim 7 in which $R_2$ is hydrogen.

9. A compound according to claim 8 in which $R_1$ is 2-trifluoromethoxy.

10. A compound according to claim 8 in which $R_1$ is 3-methoxy.

11. A compound according to claim 7 in which $R_2$ is methyl, $R_3$ is hydrogen and $R_4$ is O.

12. A compound according to claim 11 in which $R_1$ is 3-trifluoromethyl.

13. A compound according to claim 11 in which $R_1$ is 3-fluoro, 4-trifluoromethyl.

14. A compound according to claim 11 in which $R_1$ is 3-methoxy.

15. A compound according to claim 11 in which $R_1$ is 2-trifluoromethoxy.

16. A compound according to claim 11 in which $R_1$ is 2-fluoro, 3-trifluoromethyl.

17. A compound according to claim 11 in which $R_1$ is 3-fluoro.

18. A compound according to claim 11 in which $R_1$ is 3-ethoxymethyl.

19. A compound according to claim 11 in which $R_1$ is 2-methyl.

20. A compound according to claim 11 in which $R_1$ is 2-chloro.

21. A compound according to claim 11 in which $R_1$ is 2-bromo.

22. A compound according to claim 11 in which $R_1$ is 2-fluoro.

23. A compound according to claim 11 in which $R_1$ is 2-fluoro, 3-chloro.

24. A compound according to claim 11 in which $R_1$ is 2,3-difluoro.

25. A compound according to claim 11 in which $R_1$ is 3-chloro.

26. A compound according to claim 11 in which $R_1$ is 3-iodo.

27. A compound according to claim 11 in which $R_1$ is 3-trifluoromethoxy.

28. A compound according to claim 7 in which $R_2$ is ethyl, $R_3$ is hydrogen and $R_4$ is O.

29. A compound according to claim 28 in which $R_1$ is 3-trifluoromethyl.

30. A compound according to claim 28 in which $R_1$ is 3-trifluoromethoxy.

31. A compound according to claim 1 in which $R_4$ is $N-R_5$.

32. A method of controlling undesirable vegetation comprising applying to said vegetation or the locus thereof a herbicidally effective amount of a compound according to claim 1.

33. A herbicidal composition comprising:
a) A herbicidally effective amount of a compound according to claim 1; and
b) a diluent or carrier suitable for use with herbicides.

* * * * *